US010327749B1

(12) United States Patent
Passons (10) Patent No.: US 10,327,749 B1
(45) Date of Patent: Jun. 25, 2019

(54) SURGERY MANIPULATOR (71) Applicant: Leslie C. Passons, Dunlap, TN (US)

(72) Inventor: Leslie C. Passons, Dunlap, TN (US)

( * ) Notice: Subject to any disclaimer, the term of this patent is extended or adjusted under 35 U.S.C. 154(b) by 18 days.

(21) Appl. No.: 15/147,328

(22) Filed: May 5, 2016

Related U.S. Application Data (63) Continuation-in-part of application No. 14/250,429, filed on Apr. 11, 2014, now abandoned, which is a continuation-in-part of application No. 14/198,638, filed on Mar. 6, 2014, now abandoned.

(60) Provisional application No. 61/811,444, filed on Apr. 12, 2013, provisional application No. 61/787,634, filed on Mar. 15, 2013.

(51) Int. Cl.
A61B 17/02 (2006.01)
A61B 34/00 (2016.01)

(52) U.S. Cl.
CPC .......... A61B 17/0218 (2013.01); A61B 34/71 (2016.02); A61B 2017/0225 (2013.01); A61B 2217/005 (2013.01); A61B 2217/007 (2013.01)

(58) Field of Classification Search
CPC .. A61B 17/0218; A61B 2217/005–007; A61B 17/0206; A61B 2017/0025
See application file for complete search history.

(56) References Cited

U.S. PATENT DOCUMENTS

| | | | | |
|---|---|---|---|---|
| 3,667,474 A * | 6/1972 | Lapkin | ................... | A61M 29/02 606/198 |
| 5,113,846 A * | 5/1992 | Hiltebrandt | ............... | A61B 1/32 600/225 |
| 5,195,507 A * | 3/1993 | Bilweis | ............... | A61B 1/00082 600/204 |
| 5,197,948 A * | 3/1993 | Ghodsian | ......... | A61B 17/00234 604/249 |
| 5,203,773 A * | 4/1993 | Green | .................... | A61B 17/34 604/104 |
| 5,339,803 A * | 8/1994 | Mayzels | ............ | A61B 17/0218 600/201 |
| 5,345,927 A * | 9/1994 | Bonutti | ............... | A61B 17/0218 600/204 |
| 5,351,679 A * | 10/1994 | Mayzels | ............ | A61B 17/0218 600/214 |
| 5,353,784 A * | 10/1994 | Nady-Mohamed | ......................... | A61B 17/0218 600/205 |
| 5,358,496 A * | 10/1994 | Ortiz | .................. | A61B 17/0218 604/104 |
| 5,441,044 A * | 8/1995 | Tovey | ................ | A61B 17/0218 600/215 |
| 5,613,950 A * | 3/1997 | Yoon | ................ | A61B 17/00234 600/225 |
| 5,656,012 A * | 8/1997 | Sienkiewicz | ...... | A61B 17/0218 600/201 |
| 5,662,676 A * | 9/1997 | Koninckx | .......... | A61B 17/0218 600/210 |

(Continued)

Primary Examiner — Jacqueline T Johanas
(74) Attorney, Agent, or Firm — Stephen J. Stark; Miller & Martin PLLC (57) ABSTRACT A surgical manipulating instrument provides a shaft with pivoting arms operably coupled thereto to transition between an inserting configuration with the arms at least substantially parallel to the shaft and a deployed configuration with the arms fanned out to provide a paddle within a person during surgical procedures. The shaft may provide access for a suction and/or irrigation device.

9 Claims, 7 Drawing Sheets

(56) References Cited

U.S. PATENT DOCUMENTS

| | | | | |
|---|---|---|---|---|
| 5,685,826 A * | 11/1997 | Bonutti | A61B 17/0218 | 600/204 |
| 5,803,902 A * | 9/1998 | Sienkiewicz | A61B 17/0218 | 128/853 |
| 5,865,802 A * | 2/1999 | Yoon | A61B 17/00234 | 600/114 |
| 5,891,162 A * | 4/1999 | Sugarbaker | A61B 17/29 | 606/151 |
| 5,895,352 A * | 4/1999 | Kleiner | A61B 17/02 | 600/206 |
| 5,904,649 A * | 5/1999 | Andrese | A61B 17/0218 | 600/204 |
| 6,443,959 B1 * | 9/2002 | Beland | A61B 17/221 | 606/127 |
| 6,620,129 B2 * | 9/2003 | Stecker | A61M 1/0084 | 604/107 |
| 2005/0240083 A1 * | 10/2005 | Orban, III | A61B 17/0218 | 600/210 |
| 2007/0161864 A1 * | 7/2007 | Sloan | A61B 17/0218 | 600/204 |
| 2009/0182279 A1 * | 7/2009 | Wenchell | A61B 17/34 | 604/164.04 |
| 2010/0106052 A1 * | 4/2010 | Uznanski | A61B 10/04 | 600/562 |
| 2011/0022038 A1 * | 1/2011 | Seshadri | A61B 17/3207 | 606/7 |
| 2011/0105848 A1 * | 5/2011 | Sadovsky | A61B 17/0218 | 600/204 |
| 2011/0118545 A1 * | 5/2011 | Williams | A61B 1/00052 | 600/104 |
| 2012/0078059 A1 * | 3/2012 | Perez-Cruet | A61B 17/0218 | 600/210 |
| 2013/0217959 A1 * | 8/2013 | Haarstad | A61B 17/00234 | 600/37 |
| 2014/0216467 A1 * | 8/2014 | Kochem | A61B 18/1485 | 128/840 |
| 2015/0105629 A1 * | 4/2015 | Williams | A61B 1/00052 | 600/208 |

* cited by examiner

SURGERY MANIPULATOR

CLAIM OF PRIORITY

This application claims priority to U.S. patent application Ser. No. 14/250,429 filed Apr. 11, 2014, which, in turn claims the benefit of U.S. Provisional Patent Application No. 61/811,444 filed Apr. 12, 2013 and U.S. patent application Ser. No. 14/198,638 filed Mar. 6, 2014 which claims the benefit of U.S. Provisional Patent Application No. 61/787,634 filed Mar. 15, 2013. All of these references are incorporated herein by reference in their entirety.

FIELD OF THE INVENTION

The present invention relates to a manipulator for use with surgery and more particularly a manipulator for use with surgery which holds portions of the anatomy out of the way during surgical operations, preferably while still performing suction or irrigation.

BACKGROUND OF THE INVENTION

Robotic surgery has been performed for hysterectomies, prostate surgery and other procedures for many years. Companies such as Intuitive, Striker, Ethicon and others provide robotic equipment and tools for use with those procedures including robots, trocars and other devices for directing instruments into and out of the abdominal cavity for use in performing those procedures. There are non-robotic procedures to address these medical issues and others as well.

One common issue in some surgeries such as hysterectomies and prostate work is that the bladder or other organs and/or tissues can either obscure the view of the surgeon operating a robot and/or crowd the area where the doctor is working either with, or without, robotic assistance. Typically, a surgical assistant will utilize a probe suction device to push the structure out of the way such as the bladder from view. Unfortunately, the typical suction instrument often provides an elongated probe with dimensions to fit through the trocar cross section. The bladder can sometimes unfortunately migrate its way around the instrument to obscure the view or otherwise be in the way.

Accordingly, a need exists for an improved device for insertion through a trocar for surgery or other procedures to be able to use to better assist the surgeon and/or to maintain a desired field of view inside of a patient.

SUMMARY OF THE INVENTION

It is the present object of many embodiments of the present invention to provide an improved manipulator for use with surgical procedures which is particularly well adapted to be directed through trocars or other cannulated openings to then expand to a larger dimension which would not normally fit within the cross section of the trocar at its inserted end to then provide a web or at least a wider manipulator for moving and/or holding tissue, organs, and/or other material out of the way when deployed.

It is a present object of many embodiments of the present invention to provide retraction of abdominal organs in conjunction with a suction/irrigation device, or separate from a suction/irrigation device.

It is another object of many embodiments of the present invention to provide an improved device for providing an improved field of view internal to a patient during surgery techniques.

Accordingly, in accordance with a presently preferred embodiment of the present invention, a manipulator is provided which has an insertion configuration allowing the instrument to be directed through a trocar or other cannulated device such as during surgery. Once inserted, the instrument preferably has a deployed configuration in which extendable arms are extended from an insertion/retraction configuration to an extended configuration. The instrument preferably inserts through the cross section of a trocar and then is transitioned into the extended configuration whereby the inserted end fans or somehow otherwise spreads out preferably somewhat in the shape or context of a fan, possibly having a largest width at the distal or inserted end of the device while also possibly improving the function of a suction and/or irrigation device through at least a portion of the instrument. Upon completion of use, the arms can then retract back toward and/or to the insertion configuration for removal from the body to fit through the trocar.

The preferred embodiment may be designed so that it attaches to an end of a suction and/or irrigation supply. Through activation of an operator, or other mechanism(s), the arms can be deployed and retracted. Cables can pull the arms from the deployed configuration toward and/or to the insertion configuration for removal of the device. A plunger can push out arms to a wedge to effectively spread out the fan for the preferred embodiment. Other embodiments may deploy/retract differently. The Cables may also assist in deployment/retraction. Twisting shaft and/or other deployment/retraction may be used for deployment and/or retraction for other embodiments.

A paddle, such as a mesh bag over and/or between the arms and/or cables, can extend between the arms and a shaft. A webbed "foot" or paddle can provide a significantly wider cross section than a prior art probe as well as the cross section of the trocar so that the manipulator improve the field of view for a surgeon and/or keep structure out of the surgeon's way during various surgical procedures.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENT

Figure 1:
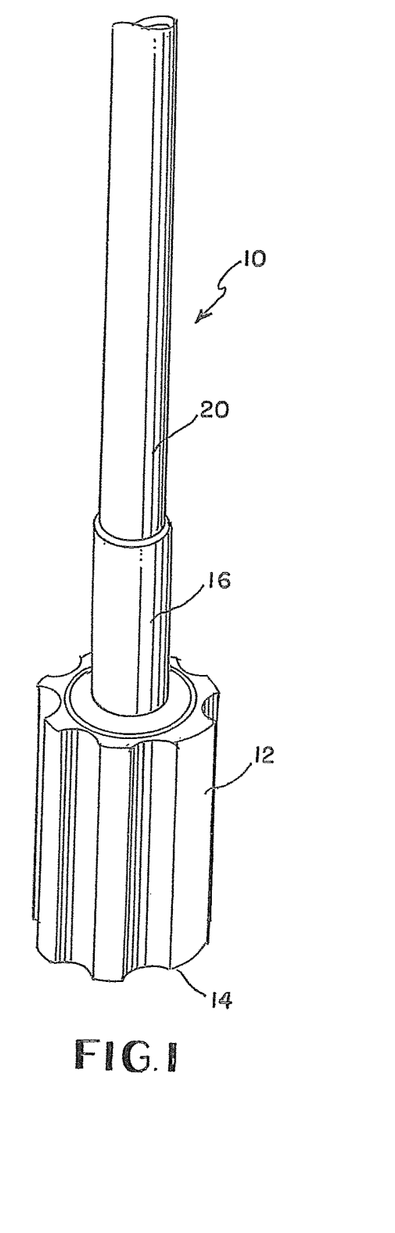
FIG. 1 is a front perspective view of a first portion of the manipulator of a presently preferred embodiment.

Accordingly, in accordance with a presently preferred embodiment of the present invention, FIG. 1 shows a front perspective view of a first portion of the presently preferred embodiment of the invention showing internals of the instrument 10 having a suction or irrigation connection 12. Irrigation connection 12 is illustrated which would connect to a vacuum supply, typically from end 14 as would be understood by those of ordinary skill in the art. The deployment system and retraction system will be described in detail below. It is important to remember that these are just two possibilities for these systems that can be used respectively. Other embodiments may utilize parts differently and/or have other components which can achieve the scope of the claims and/or be within the spirit of the invention while having different deployment and/or retraction systems.

Figure 2:
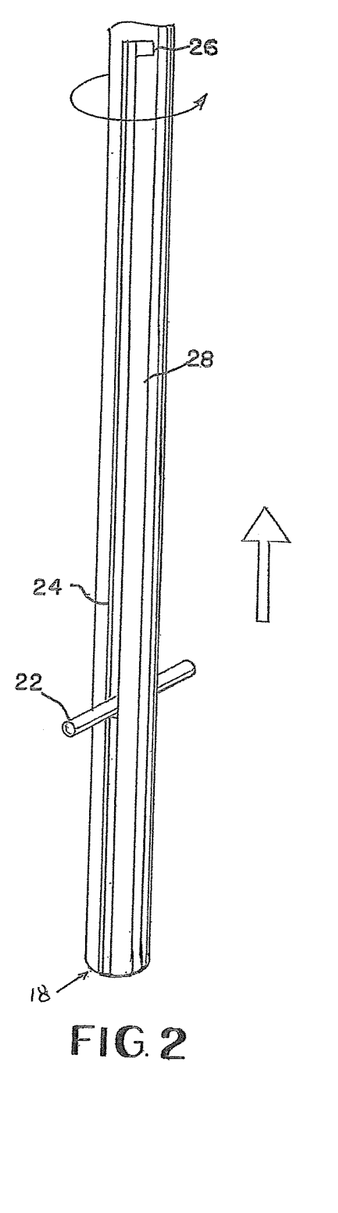
FIG. 2 is a front perspective view of a second portion of the manipulator of a presently preferred embodiment.

As shown in FIG. 1, male or other fitting 16 may have externally directed threads which may cooperate with internally directed threads, such as in female fitting 18 shown in FIG. 2. Tubing 20 may provide a bore to give access for an instrument providing either in suction or as irrigation or both depending on the embodiment. The first and second sections may be constructed in various manners or together as would be understood by those of ordinary skill in the art. The embodiment of FIGS. 12-14 may better show the bore in the tubing 20 as discussed below.

Figure 3:
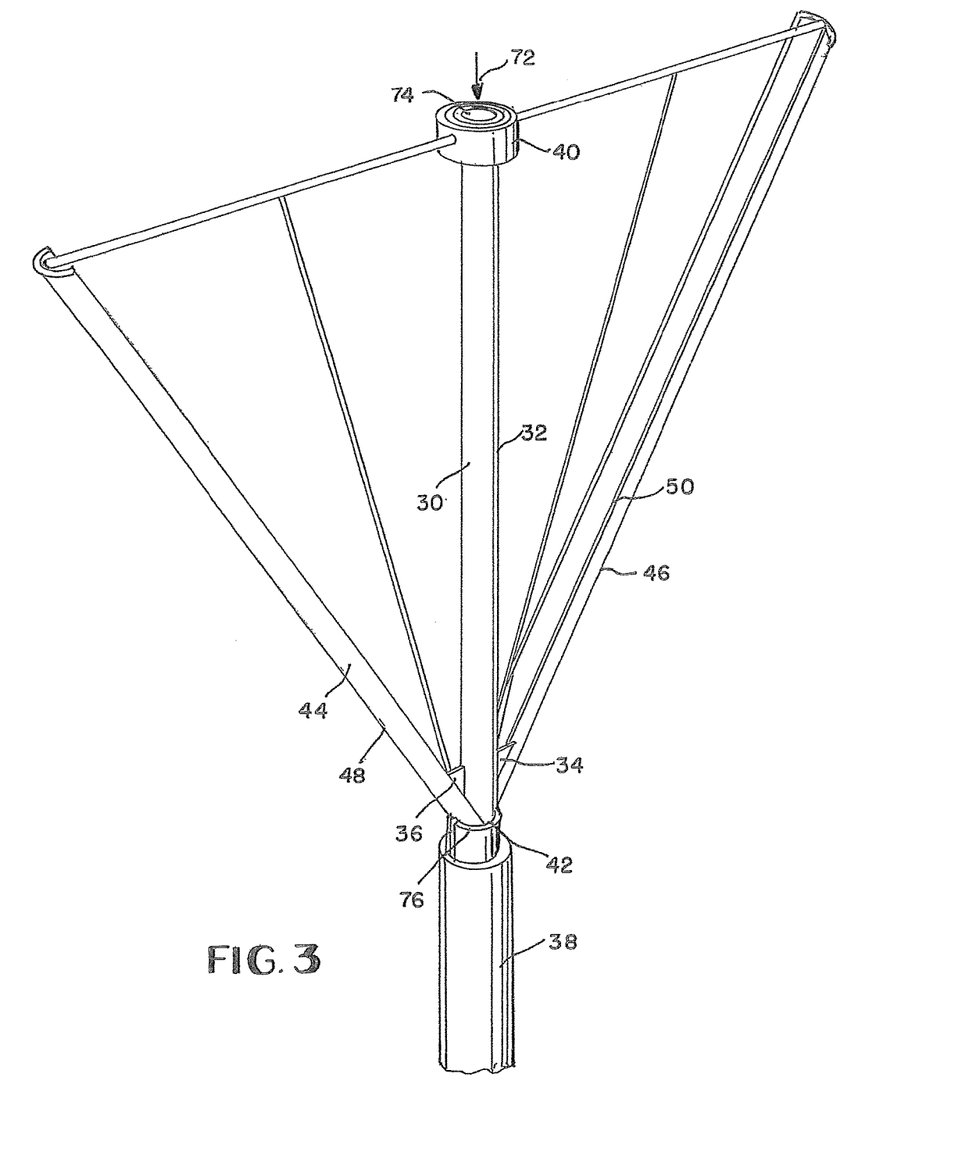
FIG. 3 is a front perspective view of a third portion of the manipulator of a presently preferred embodiment in a deployed configuration without the mesh installed.

FIG. 2 shows a second portion of the instrument 10. This portion has an operator 22 which may move relative to a slot 24 in shroud 28. Notch 26 may be provided so that operator 22 may be held or locked in place at a desired position, such as for the deployed configuration. When transitioning from the insertion configuration (shown in FIGS. 2 and 7) to the deployed configuration shown in FIGS. 2-6, the shaft 30 may or may not move depending on the design with the operator 22 or otherwise. Rods 32, 33 may be useful to connect to the operator 22 to at least assist in pushing collar 40 from lower on the shaft 30 to higher, such as illustrated in FIG. 3. A base 42 may also assist in pushing arms 44,46 upwardly from an installing configuration to the deployed configuration shown in FIG. 3. Wedges 34,36 may be accommodated by slots 48,50 until the arms 44,46 are almost fully outwardly (or upwardly) deployed relative to the sleeve 38. Then the wedges may push against abutments 52,53 (shown in FIGS. 4 and 5) to at least assist in fanning out the arms 44,46 as illustrated to the deployed configuration.

The wedges 34,36 for many embodiments can travel in slots until reaching the abutments 52,53. The wedges may or may not be fixedly connected to shaft 30.

As the operator 22 moves upwardly from the position shown in FIG. 2 in the slot 24, the extension 54 may or may not move upwardly as well as the shaft 30. For many embodiments, base 42 moves upwardly to at least assist in upwardly moving the arms 44,46 with the wedges 34,36 moving from a position higher in the slots 48,50 to lower.

Figure 6:
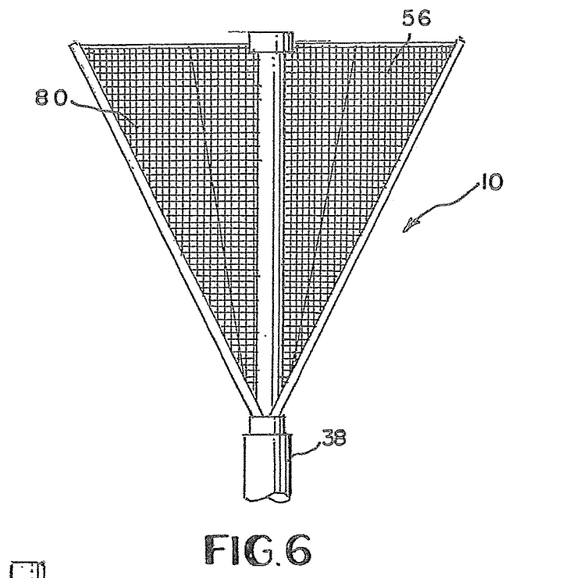
FIG. 6 is side plan view of the portion of FIGS. 3-5 with the mesh installed.
Figure 7:
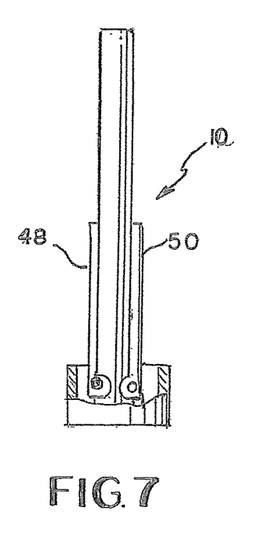
FIG. 7 is a side plan partially cut away view of the portion of FIGS. 3-5 in an install configuration.

When the wedges 34,36 contact the abutments 52,53, the arms 44, 46 can fan out for at least many embodiments. As shown in FIG. 6, material stretched across and/or between arms 44,46 can form a paddle 56 when fanned having a greater cross sectional width than the sleeve 38. More about the paddle 56 will be discussed below.

The arms 44,46 may be inserted while parallel to the shaft 30 for many embodiments thus providing a small enough cross section (particularly with respect to width) so as to be insertable through a trocar, catheter or other cannulated device with the sleeve 38. The material 80 of the paddle and cables 62-68 may be positioned at least partially internal to arms 44, 46 such as between arms 44,46 and shaft 30. The arms 44,46 may connect at pivots 58,60 or otherwise operably pivot at or just above or proximate to base 42 which may connect to operator 22.

Figures 4, 5:
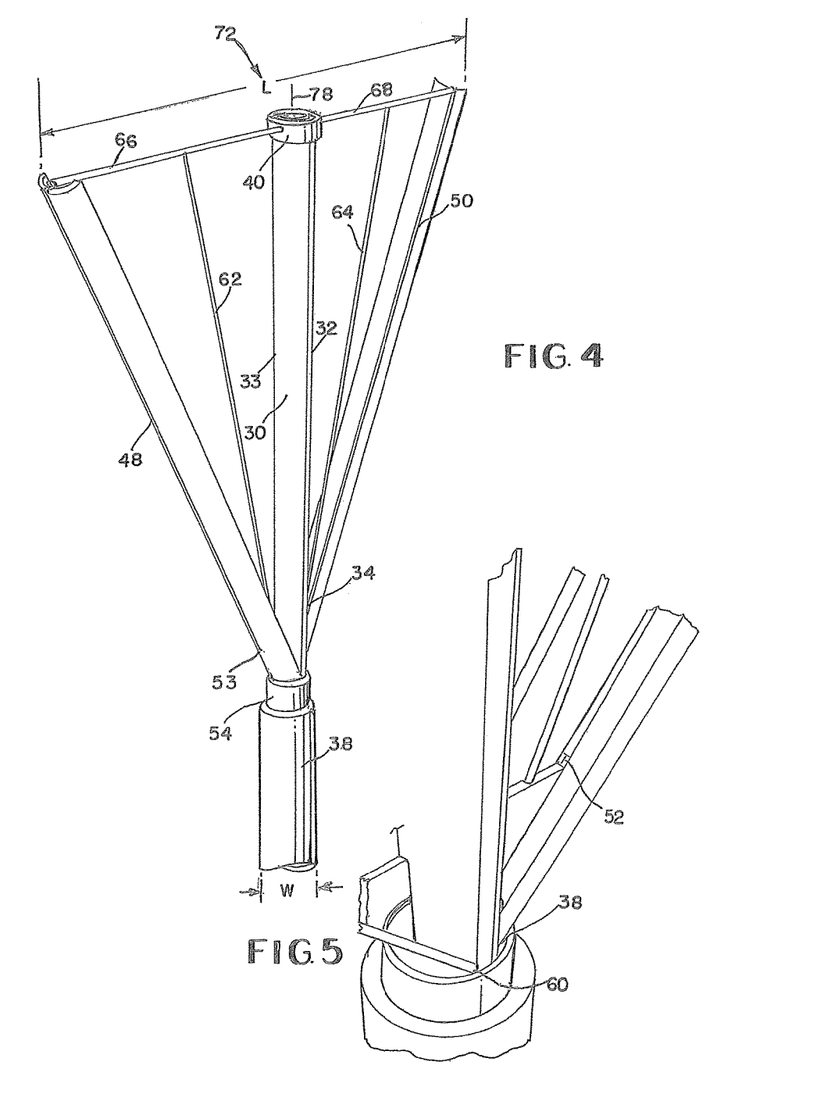
FIG. 4 is a side perspective view of the third portion of the manipulator as shown in FIG. 3.
FIG. 5 is a detailed view of a portion of FIG. 4.

FIGS. 4 and 5 show the instrument 10 with the cables 62,64 and 66,68 connected. The inserted distal end 72 has port 74 which can be used for access for irrigation as explained above. Suction is preferred for collar 40 is shown at the distal end 72. This is the deployed configuration without the paddle 56 which would obscure view. Cables 62-68 can provide a frame for supporting the paddle 56 for at least some embodiments, possibly along with shaft 30 and/or rods 32,33.

When getting ready to remove the instrument 10, such as after use, the instrument 10 may be transitioned back towards or to an insertion configuration. Operator 22 may be moved out of notch 26 and downwardly or otherwise directed in slot 24. This can direct rods 32,33 downwardly to possibly pull collar 40 downwardly. Meanwhile one or more of the cables 62-68 can possibly be pulled (such as by being connected to collar 40, wedges 34,36, base 42 or other structure so that the arms 44,46 are pulled downwardly, thus for at least some embodiments, thereby moving the arms 44,46 off of the abutments 52,53 and into the slots 48,50, thus allowing the arms 44,46 to then move against or towards the shaft 30 along with the material forming the paddle 56 and the cables 62-68. The arms 44,46 can then possibly move into the extension 54 for at least some embodiments, and for some embodiments the extension 54 may move into the sleeve 38.

FIGS. 4-6 preferably illustrate a maximum deployed configuration such as by having the arms 44,46 contact base 42 as shown. Further rotation of the arms 44, 46 may be arrested by stops 76 which may at least assist in preventing further rotation of the arms 44,46 about pivots 58,60, possibly with the cables 66,68 or other devices. This and/or other configurations may utilize the cables 62-68 to at least assist in spreading out the arms (and connected mesh or paddle 56 if utilized) or otherwise provide a frame, such as a fan like shape with the largest distance L disposed towards the proximal end 72 in the deployed configuration. Depending on the relative stiffness of the cables 62-68, or other factor they or other structure may be used to return the instrument 10 back towards or to its insertion configuration as well.

Insertion axis 78 is illustrated in FIG. 4 and is preferably parallel to the shaft 30, extension 54 and sleeve 38. During the insertion phase, in the insertion configuration the arms 44,46 are also preferably parallel to the insertion axis 78. The insertion axis 78 may also be a rotation axis for at least some embodiments.

Figure 8:
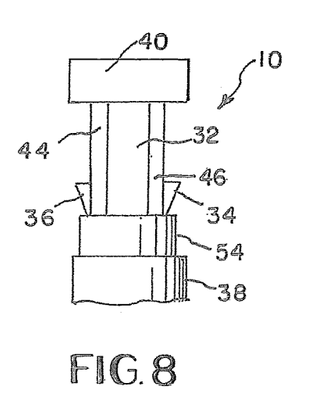
FIG. 8 is a side plan view of a portion of the embodiment shown in FIG. 3-5.

FIGS. 1-5 do not show the web or paddle 56 attached which is shown in FIG. 6 which provides a web or a net to provide wider cross section L other than just sleeve 38. Mesh 80 can extend over cables 62-68 and shaft 30 although some embodiments may be constructed differently. This embodiment may deploy to a fan configuration. Arms 44,46 may be deployable in various ways as is known in the art. The arms 44,46 are in the insertion configuration to be directed through the trocar and then retracted for removal after being used in the deployed configuration Upon retraction, the trocar or other cannulated opening, may assist cables 62-66 base 42 connected to operator 22, and/or rods 32,33 to direct arms 44,46 back to or toward the insertion configuration when withdrawing the instrument 10 from the trocar. There are various ways the arms 44,46 could be made to deploy and then retract. The width L is preferably at least twice as wide as width W of the sleeve 38 in the deployed configuration, but must be no wider than the width of the sleeve or diameter of the trocar of other cannulated opening through which it is inserted in the inserted configuration. FIG. 8 shows one insertion configuration with arms 44, 46 over the material 80 of the paddle and shaft 30 and cables 62-64. Wedges 34, 36 may or may not extend radially beyond slots 48,50 or arms 44, 46 or extension 54 or sleeve 38. Other embodiments may work differently. The collar 40 may be located internal to the arms 44, 46 in configuration for at least some embodiments. Other embodiments may be more or less compacted (or contained within arms 44, 46 and/or sleeve 38 and/or extension 54.)

As the arms 44,46 are spread out, they preferably assist in deploying the paddle 56 between the arms 44,46 and over or between shaft 30 and the arms 44,46 if so constructed. The illustrated paddle 56 is somewhat triangular shaped, but other embodiments may have other shapes. The paddle 56 and/or deployed arms 44,46 preferably have a width L greater than W when in the deployed configuration and less than W with the arms 44,46 in the insertion configuration. In fact, the length L is preferably at least 2, at least 3, at least 4, at least 5 and even up to at least 7 or more times greater than W at the proximal end than W and can taper down to W as one proceeds away from the proximal end 28 or other direction depending on the configuration chosen.

The arms 44,46 and other components may be stainless steel and/or other appropriate materials such as surgical grade plastics. The mesh 80 may be Rayon™ or other appropriate material. The material mesh 80 is preferably anchored internal to or alternatively over the arms 44,46 to ensure it is removed with the instrument 10 when removed from use and may be secured as desired to other structure of the instrument such as the shaft 30, collar 40 and/or cables 62-68.

Although the preferred embodiment fans out at the proximal end 72, other configurations could fan out at a location spaced from and even in a direction away from the proximal end 72 either towards or away from the proximal end 72. Internal to shaft 30 suction and/or irrigation may be supplied such as from a supply.

In use, the deployed tool provides a larger width L as well as cross sectional capability to assist in holding structures out of either the field of view or out of the way over than prior art probes.

Figure 9:
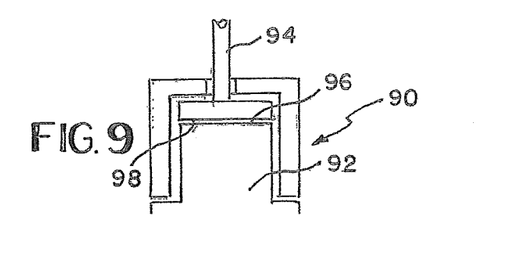
FIG. 9 is a cut away view of a slip transmission used with the embodiments of FIGS. 1-8.

FIG. 9 shows a slip transmission 90 which can be used with at least some embodiments, particularly those with operators such as operator 22 that impart twisting to shafts, such as shaft 30 or collar 40 or other portion of instrument 10 to prevent over-torquing of the arms 44,46 which assist in defining a paddle 56. As shoulder 92 is turned, it can turn arm 94 until an excessive amount or resistance is felt by arm 94 and then the friction of the faces 96,98 is overcome to prevent overtorquing of the arm 94.

Figure 10:
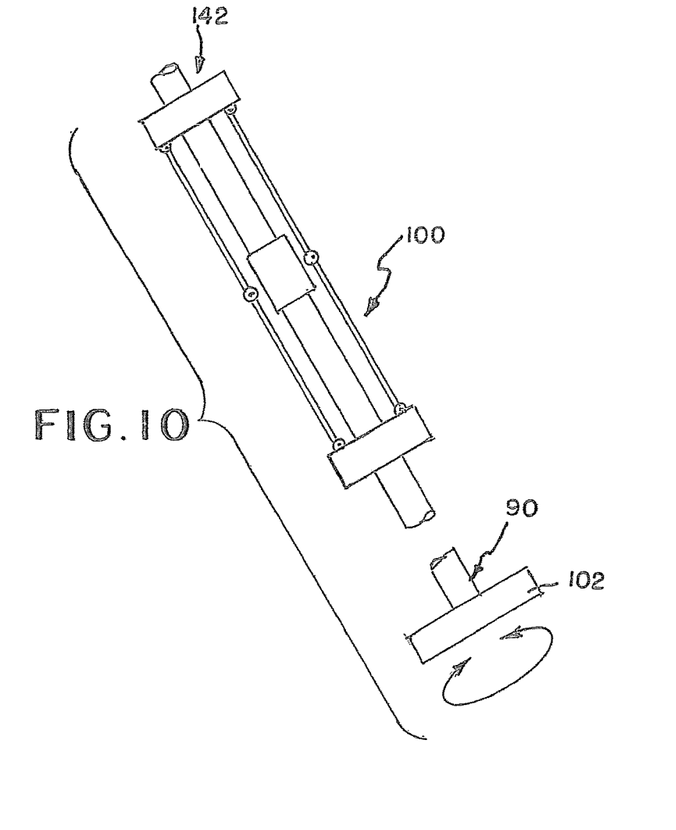
FIG. 10 is a side plan view of the first alternative of the preferred embodiment of the present invention.
Figure 11:
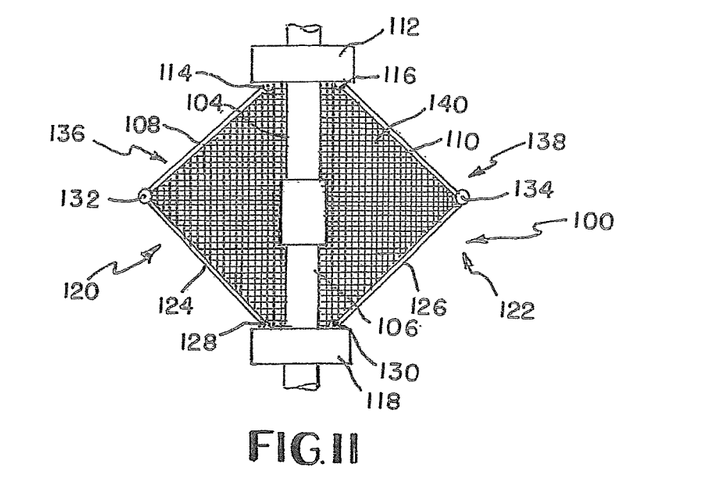
FIG. 11 is a side plan view in an extended configuration showing the embodiment of FIG. 10.

FIGS. 10 and 11 show an alternatively preferred embodiment of instrument 100. This instrument 100 has a twist operator 102 which can change a length of internal shaft 104 relative to external shaft 106 via internal threading as would be understood by those of ordinary skill in the art. Slip transmission 90 can be used at the operator 102, or other location, if at all. The arm construction is a little different than in other embodiments. First and second arms 108,110 connect to a first collar 112. The connection occurs at first and second pivots 114,116 for the preferred embodiment. As the length from the first collar 112 to second collar 118 shortens, the first and second arms pivot relative the shafts 104,106 so that ends 120,122 move away from the shaft(s) 104,106. Meanwhile, for at least some embodiments, third and fourth arms 124,126 which are connected at third and fourth pivots 128,130 may be pivotably connected at fifth and sixth pivots 132,134 to first and second arms 108,110 such as at ends 136,138. Once again as the length between the first and second collars 112,118 shortens, the arms 108,110 and 124,126 move so that ends 120,122,136, 138 move away from shafts 104,106. Other embodiments may operate differently. A web or other structure may be disposed about the arms and/or otherwise connected to the arms 108,110 and 124,126 such as with the other embodiments illustrated to form a paddle 140 possibly together with shaft(s) 104,106 when in a deployed configuration.

Paddle 140 is preferably located at or proximate to distal end 142 of device 100. In an insertion configuration, such as illustrated in FIG. 10, the arms 108,110 and 124,126 preferably are disposed within the circumference (or other perimeter) of the first and/or second collars 112,118 and/or possibly even within a perimeter of the first and/or second shafts 104,106.

Figure 12:
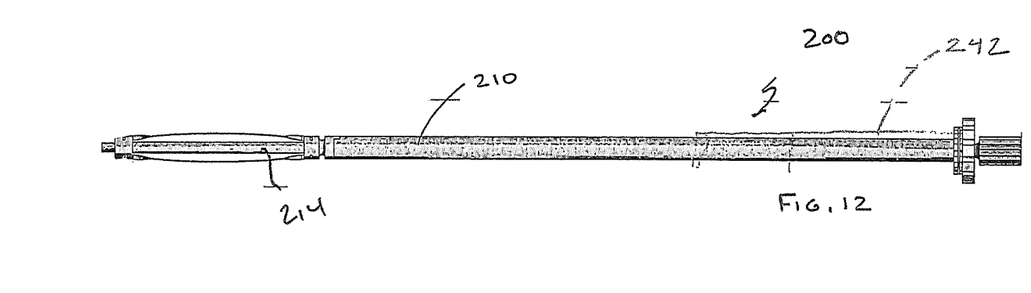
FIG. 12 is a side plan view of a second alternatively preferred embodiment of the present invention in a closed configuration.
Figure 13:
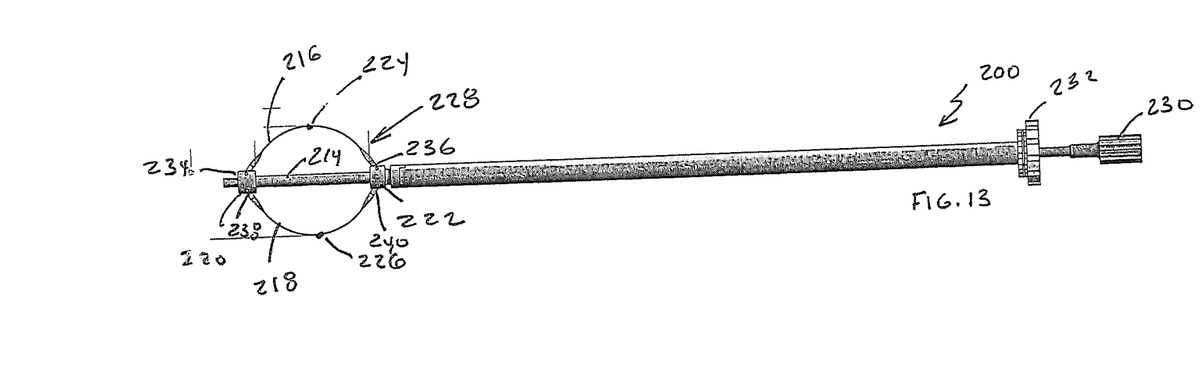
FIG. 13 is a side plan view of the embodiment of FIG. 12 in an open configuration such as could be used as a paddle inside the body (the webbing is not shown in this view)
Figure 14:
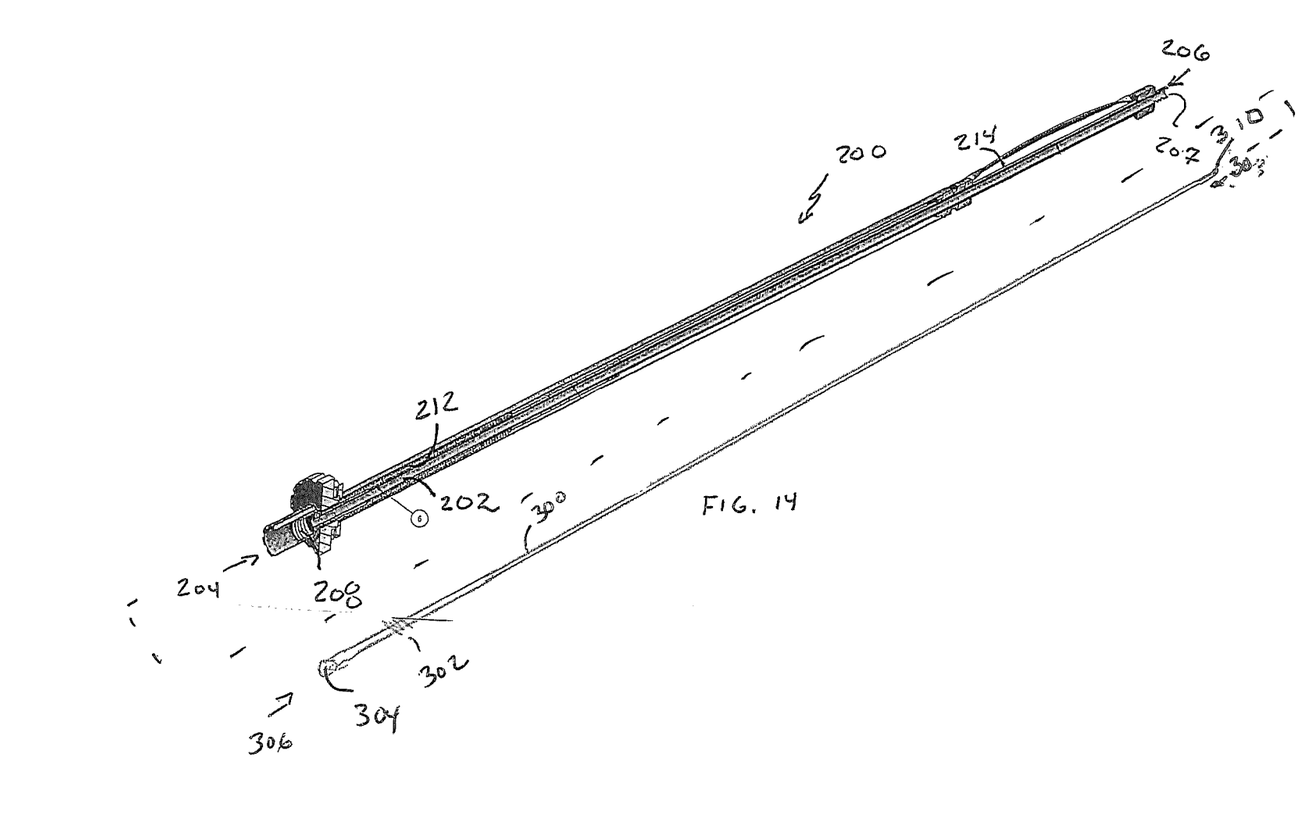
FIG. 14 is a cross sectional view of the embodiments of FIGS. 12-13 showing insertion of at least one of suction and irrigation probe through the bore of the device.

FIGS. 12-14 show another embodiment of an instrument 200 having a first end 204 and a second end 206 with a bore 202 extending from the first end 204 to the second end 206 to a port 207 for many embodiments. A first shaft 210 may have a first bore 212 which receive a suction/irrigation probe as a second shaft 214 there through. The second shaft 214 may provide the bore 202. Second shaft may provide a fitting 208 toward first end illustrated as internal threads for connecting to at least one of suction and or irrigation probe 300 such as at threads 302 as discussed above, or otherwise. The probe 300 can then reside at least partially in bore 202 when installed. Probe 300 could have an internal bore 304 to communicate at least one of suction or irrigation through bore 304 such as from toward first end 306 toward second end 308 such as from probe part 310.

FIG. 12 shows a closed configuration with spring arms 216, 218 in an elongated or non-compressed state. FIG. 13 shows a first collar 220 closer to a second collar 222 than is shown in FIG. 12 which applies compressive forces to the spring arms 216,218 preferably causing them to bow outwardly toward a center 224,226 to thus provide a paddle 228 (with a surface, such as fabric or other covering as described above or otherwise as would be understood by those of ordinary skill in the art).

Some embodiments may connect the second shaft 214 to the first collar 220 (and allow it to move relative to the second collar 222) to be able to transition from the open to the closed configurations (and visa versa), such as by using the base 230 to pull relative to boss 232 as shown when comparing FIGS. 13 to 12 (or otherwise would be understood by those of ordinary skill in the art).

Spring arms 216,218 may each connect at pivot ends 234,236 and/or 238,240 as shown or otherwise.

Sleeve 242 could be used with the instrument 200 to provide a cannulated opening into the body of a patient as shown in FIG. 12.

Second shaft 214 may be used to provide bore 202 for suction/irrigation and/or allow yet another instrument to be inserted from the first end 204 toward if not to the second end 206 (like a separate probe) for some embodiments. Various other embodiments, whether illustrated or not, could operate similarly or dissimilarly to the embodiment of FIGS. 12-14. Still other embodiments could locate port 207 at other locations and/or have a supply directed to the port 207 from a location other than first end 204. Most embodiments will likely envision the bore 202 extending the majority of the length of the instrument between first and second ends 204,206.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A surgical manipulating instrument comprising:
    an operator, said operator selectively operable between first and second positions to thereby transition the instrument between installing and deployed configurations;
    arms operably coupled to first and second collars with one of the first and second collars connected to a shaft, said arms disposed at least substantially parallel to the shaft in the installing configuration, said arms extending readily outwardly intermediate the first and second collars relative to the shaft to at least partially assist in providing a paddle extending intermediate the collars and the arms with the shaft intermediate the arms in the deployed configuration and providing a maximum width intermediate the collars in the deployed configuration with the first and second collars closer together in the deployed configuration than in the installing configuration, and another of the first and second collars operably coupled to and moving linearly relative to the shaft between the deployed and the installing configuration, and the arms which comprise first and second arms are directly connected to the first collar; and
    a port at a distal end of a bore, said port distally disposed relative to the arms of the paddle at a fixed distance from the operator, the bore extending through the operator, and the operator extending through the shaft; and
    a probe, said probe selectively directable through the bore of the operator from a removed configuration to a fully inserted configuration relative to the shaft with a terminal end of the bore a fixed distance from the operator in both the installing and deployed configurations, said probe being secured to the operator in the fully inserted configuration and said probe providing irrigation internally through the probe to discharge out of the port from a supply.

2. The surgical manipulating instrument of claim 1 wherein the paddle provides a web between the arms in the deployed configuration.

3. The surgical manipulating instrument of claim 2 wherein the web is comprised of a mesh material.

4. The surgical instrument of claim 1, wherein said first collar is connected to the shaft and the arms and movement of the operator moves the first collar towards the second collar transitioning the instrument between the installing and the deployed configuration.

5. The surgical instrument of claim 4 wherein the arms are pivotably connected at a first ends of the arms to the first collar and are coupled to the second collar through second ends opposite the first ends.

6. The surgical instrument of claim 1 wherein the arms are pivotably connected relative to the shaft at first ends of the arms.

7. The surgical instrument of claim 1 further comprising a sleeve and an extension between the sleeve and the shaft.

8. The surgical instrument of claim 1 further comprising a sleeve about at least a portion of the shaft, said sleeve received within a cannulated opening in a body of a person when installed during surgery with the arms extending a width less than a width of the sleeve in the installing configuration and having a width of at least about three times the width of the sleeve in the deployed configuration.

9. The surgical instrument of claim 8 when the second collar is located within the sleeve.

* * * * *